United States Patent
Trotter et al.

(10) Patent No.: US 10,190,963 B2
(45) Date of Patent: Jan. 29, 2019

(54) METHODS AND SYSTEMS FOR ASSESSING SAMPLE BEHAVIOR IN A FLOW CYTOMETER

(71) Applicant: Becton Dickinson and Company, Franklin Lakes, NJ (US)

(72) Inventors: Joseph Trotter, La Jolla, CA (US); Sujata Iyer, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 497 days.

(21) Appl. No.: 14/170,409

(22) Filed: Jan. 31, 2014

(65) Prior Publication Data

US 2014/0216128 A1    Aug. 7, 2014

Related U.S. Application Data

(60) Provisional application No. 61/759,878, filed on Feb. 1, 2013.

(51) Int. Cl.
*G01N 33/48* (2006.01)
*G01N 15/14* (2006.01)
*G06G 7/58* (2006.01)
*G01N 15/10* (2006.01)

(52) U.S. Cl.
CPC ..... *G01N 15/1459* (2013.01); *G01N 15/1404* (2013.01); *G01N 2015/1006* (2013.01); *G01N 2015/149* (2013.01)

(58) Field of Classification Search
CPC ................ G01N 2015/14021; G01N 15/147
See application file for complete search history.

(56) References Cited

U.S. PATENT DOCUMENTS

| | | | |
|---|---|---|---|
| 5,466,572 A | 11/1995 | Sasaki et al. | |
| 5,817,519 A * | 10/1998 | Zelmanovic et al. | 436/63 |
| 6,555,360 B1 | 4/2003 | Srienc et al. | |
| 8,140,300 B2 | 3/2012 | Dunne et al. | |
| 8,570,512 B2 | 10/2013 | Schilffarth | |
| 2001/0006416 A1 | 7/2001 | Johnson | |
| 2006/0141628 A1 | 6/2006 | Evans | |
| 2010/0248362 A1 | 9/2010 | Durack et al. | |
| 2010/0319469 A1 | 12/2010 | Rich | |
| 2012/0148142 A1 | 6/2012 | Ortyn et al. | |

FOREIGN PATENT DOCUMENTS

| | | |
|---|---|---|
| EP | 1 892 523 | 2/2008 |
| WO | WO 2012/148584 | 11/2012 |

OTHER PUBLICATIONS

International Search Report for International Application No. PCT/US14/14273 dated Aug. 13, 2014.
Bauer et al. (eds.), Clinical Flow Cytometry: Principles and Applications, Williams & Wilkins (1993).
Jaroszeski et al. (eds.), Flow Cytometry Protocols, Methods in Molecular Biology No. 91, Humana Press (1997).
Landy et al. (eds.), Clinical Flow Cytometry, Annals of the New York Academy of Sciences vol. 677 (1993).
Lindmo et al. "Measurement of the Distribution of Time Intervals between Cell Passages in Flow Cytometry as a Method for the Evauluation of Sample Preparation Procedures." Cytometry. vol. 2. No. 3. pp. 151-154 (1981).
Ormerod (ed.), Flow Cytometry: A Practical Approach, Oxford Univ. Press (1997).
Pinkel D. and Stovel, R. 1985 'Flow Chambers and Sample Handling', in *Flow Cytometry : Instrumentation and Data Analysis* (van Dilla, M.A., Dean P.N., Laerum, O.D., and Melamed M.R., eds) Academic Press, London pp. 77-128.
Practical Shapiro, Flow Cytometry, 4th ed., Wiley-Liss (2003).
Pawley (ed.), Handbook of Biological Confocal Microscopy, 2nd Edition, Plenum Press (1989).
Supplementary European Search Report for Application No. EP 14 74 6564 dated Oct. 6, 2016.

* cited by examiner

*Primary Examiner* — Eric S DeJong
(74) *Attorney, Agent, or Firm* — Knobbe Martens Olson & Bear LLP

(57) ABSTRACT

Methods and systems are disclosed for generating an entrainment factor in a flow cytometry sample. The methods comprise flowing a sample with a series of particles through the flow cytometer, detecting events and calculating an expected frequency of those events based on a distribution, such as a Poisson distribution, and measuring an observed frequency of particle events. An entrainment factor may be generated from a ratio of observed event frequency to expected event frequency. Further adjustment to the flow cytometer maybe performed based on the indicated entrainment factor such as adjusted sorting bias.

7 Claims, 8 Drawing Sheets

METHODS AND SYSTEMS FOR ASSESSING SAMPLE BEHAVIOR IN A FLOW CYTOMETER

CROSS-REFERENCE TO RELATED APPLICATIONS

This application claims priority benefit under 35 U.S.C. § 119(e) to U.S. Provisional Application No. 61/759,878, filed on Feb. 1, 2013, entitled "Methods and Systems for Assessing Sample Behavior in a Flow Cytometer," the disclosure of which is hereby incorporated by reference in its entirety. Any and all priority claims identified in the Application Data Sheet, or any correction thereto, are hereby incorporated by reference under 37 C.F.R. § 1.57.

BACKGROUND

Technical Field

This disclosure relates to relates generally to the field of flow cytometry and more particularly to sample analysis methods.

Background

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Cytometers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

Fluorescence-activated cell sorting or particle sorting is a specialized type of flow cytometry. It provides a method for sorting a heterogeneous mixture of particles into two or more containers, one cell at a time, based upon the specific light scattering and fluorescent characteristics of each cell. It records fluorescent signals from individual cells, and physically separates cells of particular interest. The acronym FACS is trademarked and owned by Becton Dickinson.

The particle suspension is placed near the center of a narrow, rapidly flowing stream of liquid. The flow is arranged so that on the average (Poisson distribution) there is a large separation between particles relative to their diameter. A vibrating mechanism causes the stream of particles to break into individual droplets. The system is adjusted so that there is a low probability of more than one particle being in a droplet. Just before the stream breaks into droplets the flow passes through one or more laser intersects where the fluorescent character of interest of each particles are measured. If a particle is to be collected, a charge is applied to the flow cell during the period of time one or more drops form and break off from the stream. These charged droplets then fall through an electrostatic deflection system that diverts droplets into target containers based upon the charge applied to the droplet.

A sample can include thousands if not millions of cells. Cells may be sorted to purify a sample to the cells of interest. The sorting process can generally identify three varieties of cells: cells of interest, cells which are not of interest, and cells which cannot be identified. In order to sort cells with high purity (e.g., high concentration of cells of interest), droplet generating cell sorters typically abort cells that are too close to another unwanted cell electronically and thereby reduce contamination of the sorted populations. Highly discriminate sorting can lead to a reduced number of cells for analysis. In addition, the time needed to perform the detailed sorting may be higher than less strict sorting.

Furthermore, in samples of adherent cells, or antigen presenting cells such as monocytes and dendritic cells or those that have been processed in a manner that increases cell to cell interaction, this can often lead to poor recovery. In a well dispersed sample, the distribution of cells is random and follows the statistics of a Poisson distribution. As noted by Lindmo (1981) by measuring the time interval between events it is possible to evaluate the deviation from the ideal distribution. Accordingly there is a need to assess in 'real time' sample behavior to determine whether a sample is well distributed.

SUMMARY

The systems, methods, and devices of the disclosure each have several innovative aspects, no single one of which is solely responsible for the desirable attributes disclosed herein.

In one innovative aspect, a method for generating an entrainment factor for a flow cytometer sample is provided. The method includes flowing the sample comprising a series of particles through the flow cytometer wherein each particle is associated with a signal. The method includes detecting a series of events with a detection system in a first time interval from a stream formed from the flow cytometer. The method further includes calculating an expected frequency of events in the first time interval based on a characterizing distribution such as a homogenous Poisson distribution. The method also includes measuring an observed frequency of events within a second time interval, wherein the second time interval is within the first time interval. The method includes generating the entrainment factor based at least in part on a ratio of the observed frequency to the expected frequency.

In another innovative aspect, a method for generating sample behavior information for a flow cytometer sample is provided. The method includes flowing the sample comprising a series of particles through the flow cytometer wherein each particle is associated with an event and the particles are distributed in a fluidic stream. The method includes detecting a series of events and a corresponding arrival time for each event. The method includes determining a series of inter-arrivals times relative to a previous event within the series and an associated probability of occurrence of the inter-arrival times relative to a length of a specified time interval. The method also includes calculating an expected frequency of events over the series of inter-arrival times for a portion of the fluidic stream having a length equal to the specified time interval, the calculating based on a predetermined distribution such as a Poisson distribution. The method includes measuring an observed frequency of events over the series of inter-arrival times within the portion of the fluidic stream. The method also includes generating the sample behavior information based at least in part on a ratio of the observed frequency to the expected frequency of events over the series of inter-arrival times for the portion of the fluidic stream.

In either of the innovative methods described, the stream may be comprised of regularly spaced droplets. In some implementations of the methods, the method may include comparing the entrainment factor to a predetermined value (e.g., greater than 1) and actuating a corrective action in a control system operationally connected to the flow cytometer based on a result of the comparing. An example of a corrective action includes halting the flow of the sample in the flow cytometer.

Some implementations of the method may include sorting particles in the stream. In such implementations, the corrective action may include adjusting the sorting based on the entrainment factor.

The innovative methods may generate the entrainment factor while the sample is flowing in the flow cytometer.

Time intervals in accordance with the innovative methods may be measured in a variety of ways. One example time interval unit is fractions of a droplet.

In some implementations, the entrainment factor is one of a plurality of entrainment factors calculated during successive time intervals for a flow cytometer sample.

The sample may include multiple labeled particles. For example, the sample may include peripheral blood cells wherein the peripheral blood cells as are comprised of a first and second component labeled with a first and second label. In implementations with multiple components, it may be desirable to generate an entrainment factor for each component. In such implementations, the method may include generating the entrainment factor for the first component and another entrainment factor for the second component.

In a further innovative aspect, a flow system for providing a sample entrainment factor is provided. The system includes a fluidics system. The fluidics system may include a sample tube and a moving fluid column within the sample tube in which particles of a sample move along a common sample path. The system includes a detection system for collecting a signal from each particle as it passes one or more detection stations along the common sample path. Each signal is assigned a signal value to form a data point for each particle. The detection system collects a succession of such data points in a first time interval. The system includes a control system operationally associated with the fluidics system. The control system is configured to generate a calculated signal frequency for at least a portion of the first time interval based on a Poisson distribution and the number of data points collected by the detection system during the first time interval. The control system is further configured to generate an experimental signal frequency based on the number of data points in the portion of the first time interval. The control system is further configured to compare the experimental signal frequency with that of a calculated signal frequency or a predetermined signal frequency. The control system is also configured to provide an entrainment factor for the sample, said entrainment factor based on said comparing.

The flow system may compare the experimental signal frequency by determining a ratio of the experimental signal frequency to that of the calculated signal frequency or the predetermined signal frequency.

In some implementations, the control system may, upon determining that the entrainment factor deviates from a predetermined value, actuate a corrective action. Corrective actions may include interrupting collection of signals by the detection system, purging the sample tube by said fluidics system, altering collection of signals via acoustic focusing based on the entrainment factor, and resuming collection of the signals by the detection system. Resuming collection of the signals may occur after initiating dispersion of the sample.

In some implementations, the control system includes a first sorting configuration providing a high collection yield and a second sorting configuration providing a high collection purity. The control system may be configured to select one of the first sorting configuration or the second sorting configuration based on the entrainment factor.

In a further innovative aspect, a non-transitory computer readable medium including instructions executable by a processor of an electronic device may be provided. The instructions, upon execution by the processor, may cause the electronic device to perform one or more of the innovative methods described above.

BRIEF DESCRIPTION OF DRAWINGS

Several advantages of the present invention will be apparent upon consideration of the following detailed description taken in conjunction with the accompanying drawings, in which.

DETAILED DESCRIPTION

Figure 1:
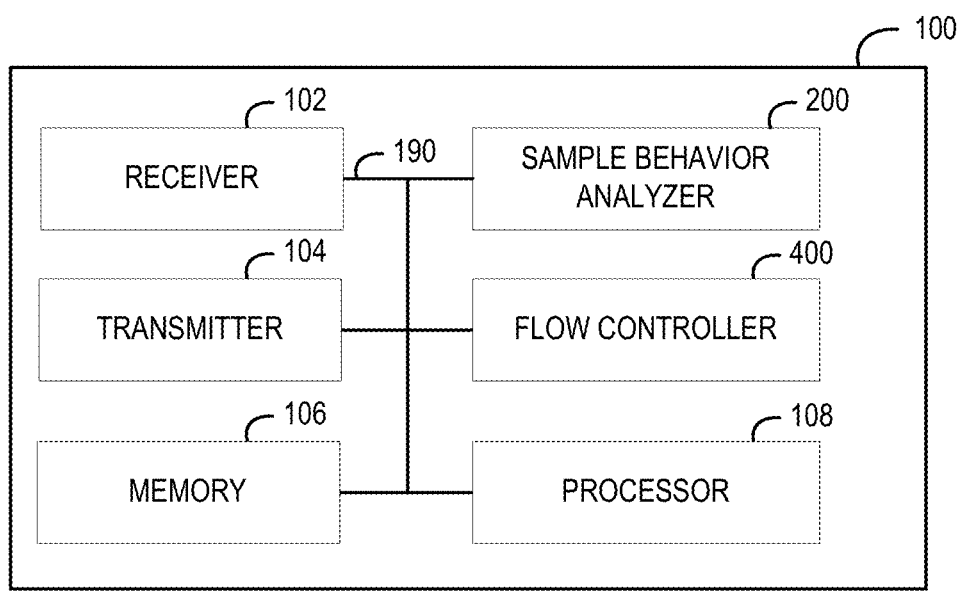
FIG. 1 shows a functional block diagram for one example of an electronic device for processing cytometry data behavior information.

The features described allow assessment, either automated or manually, of sample behavior using a simplified dispersion index. One aspect included to facility the assessment is an "entrainment factor." When analyzing different samples, the utility of the disclosed features provide a non-limiting advantage of distinguishing detected sample performance characteristics arising from sample behavior from those intrinsic to the sorter.

The present invention describes methods and systems for determining an entrainment factor in a flow cytometer sample comprising flowing a sample comprising a series of particles through the flow cytometer wherein each particle is associated with a signal and the particles are distributed in a fluidic stream that in some embodiments ultimately forms a series of regularly spaced droplets, detecting a series of signals with an inter-arrival time relative to the previous particle with the probability of occurrence relative to the length of a specified time interval, calculating the expected frequency of events in the time interval based on an Poisson (such as an ideal homogenous Poisson) distribution, measuring the observed frequency of events within a that time interval, and calculating a first entrainment factor wherein the first entrainment factor is determined from the ratio of observed frequency to expected frequency.

In some embodiments method further comprises actuating a corrective action in a control system operationally connected to the flow cytometer when the entrainment factor deviates from a predetermined value such as greater than 1. In some embodiments the corrective action may comprise halting the flow of the sample in the flow cytometer, purging the flow cytometer, initiating a user interface signal or the like. The entrainment factor may be calculated while the sample is flowing in the flow cytometer, or after the flow is completed. In some embodiments the time intervals are measured in fractions of a drop. In some embodiments the first entrainment factor is one of a plurality of entrainment factors calculated during successive time intervals for a flow cytometer sample. The sample may comprise a biological sample such as peripheral blood cells.

Some implementations may include a fluidics system comprising a sample tube and a moving fluid column within the sample tube in which particles of a sample move along a common sample path. The fluidics system may also include a detection system for collecting a signal from each particle as it passes one or more detection stations along the common sample path, each signal being assigned a signal value to form a data point for each particle. The detection system may collect a succession of such data points in a first time interval. A control system may be operationally associated with the fluidics system. The control system may be configured to calculate at least a calculated signal frequency for a second time interval based on a Poisson distribution and the number of data points collected by the detection system during the first time interval and an experimental signal frequency based on the number of data points in the second time interval. The control system may be further capable of comparing the experimental signal frequency with that of a calculated signal frequency or a predetermined signal frequency in order to determine an entrainment value. The entrainment value may be determined based on the ratio of the experimental signal frequency to that of calculated signal frequency or the predetermined signal frequency wherein the second time interval is a subset of the first time interval. In some embodiments the entrainment value may deviates from a predetermined value and the control system may actuate a corrective action. The corrective action may be any action such as carrying out one or more cycles of interrupting collection of signals by the detection system, purging the sample tube by said fluidics system, and resuming collection of the signals by the detection system. In some embodiments resuming collection of the signals occurs after steps are taken to disperse the sample. Sample dispersion may be by any means such as acoustic focusing.

Aspects described herein provide systems and methods to assess sample behavior using a dispersion index and the concept of "entrainment factor" as a metric for sample quality. Systems and methods are demonstrated using different samples, and the utility of this tool in distinguishing performance issues arising from sample behavior from those intrinsic to the sorter is discussed. Implementations including one or more of the described features serve as an effective means to generally analyze data (e.g., cytometer data) to determine how "Poisson" a population actually is during a cell sorting or analysis process, thereby serving as a metric to aid in improvement of sample preparation. Aspects described may also be used to inform a user on why a classified population may be exhibiting poor performance and contributing to a disappointing sort yield.

As used herein, the terms set forth with particularity below have the following definitions. If not otherwise defined in this section, all terms used herein have the meaning commonly understood by a person skilled in the arts to which this invention belongs.

As used herein, "system" and "instrument" and "apparatus" generally encompass both the hardware (e.g., mechanical and electronic) and associated software (e.g., computer programs) components.

As used herein, "Poisson distribution" refers to a discrete frequency distribution that indicates the probability of a number of independent events occurring in a fixed time.

As used herein, "entrain" identifies the degree of aggregation, clumping or other non-random association of particles.

As used herein, an "event" generally refers to the data measured from a single particle, such as cells or synthetic particles). Typically, the data measured from a single particle are include a number of parameters, including one or more light scattering parameters, and at least one fluorescence intensity parameters. Thus, each event is represented as a vector of parameter measurements, wherein each measured parameter corresponds to one dimension of the data space.

As used herein, a "population", or "subpopulation" of particles, such as cells or other particles, generally refers to a group of particles that possess optical properties with respect to one or more measured parameters such that measured parameter data form a cluster in the data space. Thus, populations are recognized as clusters in the data. Conversely, each data cluster generally is interpreted as corresponding to a population, although clusters that correspond to noise or background typically also are observed. A cluster may be defined in a subset of the dimensions, e.g., with respect to a subset of the measured parameters, which corresponds to populations that differ in only a subset of the measured parameters.

As used herein, a "gate" generally refers to a set of boundary points identifying a subset of data of interest. In cytometry, a gate may bound a group of events of particular interest. As used herein, "gating" generally refers to the process of classifying a population by defining a gate for a given set or subset of data.

As briefly discussed above, dot-plots are one way to visualize the data produced by the cytometer. When displaying and analyzing data, histogram, bin plot, 2D density, and/or contour plots may also be used.

The sorting of cells from a flow cytometer is a challenging task, made more so by the tendency of some cell preparations to result in the clumping or aggregation of cells or particles. Sorting efficiency in a series of droplets from a flow cytometer may show Poisson distribution in an ideal scenario, where the efficiency can be estimated by Equation (1) below:

$$\text{Efficiency} = e^{-\left(rate*(1-fraction)*\frac{d}{f}\right)} \quad (1)$$

where: d is the drop packet defined as the time in drop units;
f is the frequency of the drop drive in drops per second;
rate is the sample rate in events per second; and
fraction represents the portion of all events for the population of interest.

Many samples processed through a flow cytometer do not show a Poisson distribution. Without being bound to a particular theory, a non-Poisson distribution may be the result of many factors such as the entrainment (or clumping) of cells. It is not uncommon for investigators to "lose" a larger portion of cells than had been expected or desired due to an undesirable entrainment of desired cells with unwanted cells. In some embodiments, measurement of how "Poisson" a sample may actually be can be achieved by determining a variance from homogenous Poisson behavior for a series of events detected by flow cytometry. In one implementation, where the variance to mean ratio is 1.0, then the sample may be identified as behaving in a Poisson manner.

In some embodiments a sample may contains two or more particle types (e.g., monocytes, lymphocytes or any other cellular component) and each particle type may be labeled in a manner that provides for a distinct detectable signal. The different cellular components of a sample may exhibit different aggregation behavior. The aspects described may provide for the determination of specific entrainment factors for each distinct signal generating particle. As one non-limiting benefit, these features provide a way to understand of the behavior of distinct populations of particulates or cellular types in a sample.

In some embodiments the observed number of events within a given time interval is measured. The expected frequency of events in the same time interval is calculated based on an ideal Poisson distribution. By calculating the ratio of observed events to expected frequency of events for this or any other time interval we may obtain an "entrainment factor." This value identifies a measure of the dumpiness of the sample and the deviation from Poisson. The greater level of dumpiness indicated by the entrainment factor, the worse the sample behavior in flow.

Accordingly, the expression of the entrainment factor may be implemented in a variety of ways. For example, in one implementation a factor of 1.0 indicates Poisson samples while a factor greater than 1.0 identifies clumpy/entrained samples. In another implementation, the factor may be expressed with a zero base. In such an implementation a factor of 0 may indicate no clumps (e.g., Poisson) while positive values indicate a degree of dumpiness. In some implementations, level of dumpiness may be scaled, such as to 100. In such implementations, the factor may indicate a percent dumpiness for a sample. In some implementations, higher numerical values may indicate more Poisson samples and the lower the value the higher the dumpiness. The discussion here should highlight that the expression of the entrainment factor may be accomplished in a variety of ways without departing from the spirit of the entrainment factor which is to convey an indication of dumpiness.

Particle arrival time may be measured with a high degree of accuracy using intrinsic time stamps in firmware with a specified drop resolution. For example from $\frac{1}{16}^{th}$ of a drop, arrival time may be measured to 1.5625 microseconds at 40 KHz using BD Influx™ cell sorter available from Becton, Dickinson and Company, to 0.1 microseconds using BD FACSAria™ III cell sorter available from Becton, Dickinson and Company, or to 17.625 nanoseconds represented via a 48 bit time stamp using BD FACSJazz™ cell sorter also available from Becton, Dickinson and Company.

The arrival time may be included in the event frame of each processed event as a time stamp. In some implementations, such as in the case of the Influx™ or FACSJazz™, additional information may be provided such as the distance to the previous event in time. The data may be binned and fitted as a Poisson exponential distribution. The probability of another event occurring within time bins related to drop boundaries can then be obtained based on traditional Poisson estimates (Pinkle and Stovel, 1985). A ratio of observed probability versus an expected probability for different relevant time spans provided an "entrainment factor" metric. As discussed, one example entrainment factor is such that the result would be 1.0 for true Poisson distributions and significantly greater for those particles that entrain in a non-random manner.

The behaviors of different sample/cell types, and of subpopulations within heterogeneous samples such as peripheral blood mononuclear cells (PBMCs), show entrainment behaviors in flow that range from true homogenous Poisson distributions to non-random entrainment significantly affecting sorting performance and reducing sort yield (e.g., number of cells for which a sorting decision was reached). Consider one sample which, in applying Equation (1), can have the efficiency expression shown in Equation (2).

$$p = 1.0 - e^{\frac{-rd}{f}} \quad (2)$$

In the example sample the expected rate r is 714 events per second for a drop packet d of 1 at the frequency f of 40,400 Hz. In this example, there is only one population of interest and thus, the fraction term is not necessary. Event data for a sample can be acquired from the cytometer during a test. In one sample, we observed 829 events with delta times of 1 drop or less in sample of 10,000 events. The delta time represents a period of time for a given event to a previous event. In some implementations, the delta time measures the time to a previous event of the same type (e.g., same particle detection). In some implementations, the delta time measures the time to the previous event, irrespective of event type. In the example discussed above, the unit of time used is the number of drops. Units such as microseconds, absolute time, or other representations of time may be used within the methods and systems described. The resulting frequency for the observed sample is 0.0829. However, 175 events out of 10,000 (e.g., 0.0175*10000) with a delta time of 1 drop or less is expected based on a Poisson distribution of events and a sample rate of 714 per second.

By this example, the observed probability is 0.0829 while the expected probability for a Poisson distribution is 0.0175. In implementations where the entrainment factor is expressed as a ratio of the observed probability to the expected probability, the entrainment factor would be 0.0829/0.0175 or 4.73. If the sample exhibited the expected distribution, the ratio would yield an entrainment factor of 1.0 (e.g., 0.0175/0.0175). However, in the example sample discussed above, the entrainment factor is 4.73, nearly five-fold larger than if a homogenous Poisson process were in play.

FIG. 1 shows a functional block diagram for one example of an electronic device for processing cytometry data behavior information. The electronic device 100 may be configured to implement one or more aspects of the processes described herein.

In some implementations, the electronic device 100 may be a cytometer. It will be appreciated that other elements included in such an implementation are not shown in FIG. 1. In some implementations, the electronic device 100 may be configured to communicate with a cytometer to provide behavior analysis and control messages based thereon.

To facilitate communication with a cytometer, the electronic device 100 includes a receiver 102. The receiver 102 is configured to receive information for further processing by the electronic device 100 such as sample behavior analysis. The receiver 102 may receive raw flow cytometry data. The receiver 102 may also receive parameters to control the operational characteristics of the electronic device 100. The receiver 102 may be configured to receive messages from another electronic device such as a tablet computer, a personal computer, or a smartphone.

The receiver 102 may be implemented as a wired or wireless receiver. In a wireless implementation, the receiver 102 may include an antenna and a signal processor. In a wired implementation, the receiver 102 may include one or more of a network interface, physical connections (e.g., Ethernet, USB, HDMI, telephone, etc.), and an application programming interface to the various features described.

To further facilitate communications with a cytometer and other electronic processing systems, the electronic device 100 may include a transmitter 104. The transmitter 104 may be configured to transmit information generated or otherwise acquired by the electronic device 100. One example of information that may be transmitted by the transmitter 104 is behavior analytics such as an entrainment factor and/or actuation messages based thereon.

The transmitter 104 may be configured to format the data for transmission. The formatting may include one or more of packetization, encapsulation (e.g., in a machine readable format such as XML; JSON; delimited text; binary format such as bitmap or other image file format; and the like), encryption, and compression.

The transmitter 104 may be configured for wired or wireless transmission. In a wireless implementation, the transmitter 104 may include a signal generator, amplifier, and antenna. In a wired implementation, the transmitter 104 may include one or more of a network interface and physical connections (e.g., Ethernet, USB, HDMI, telephone, etc.).

The electronic device 100 may include a memory 106. The memory 106, which may include read-only memory (ROM) and/or random access memory (RAM), may store information received by the electronic device 100. The memory 106 may also store information generated by the electronic device 100. A portion of the memory 106 may also include non-volatile random access memory (NVRAM).

The electronic device 100 may also include a processor 108. The processor 108 may control and/or coordinate operation of the electronic device 100. In some implementations, the processor 108 may be referred to as a central processing unit (CPU). The processor may be configured to transmit messages to one or more of the components of the electronic device 100. The processor may also be configured to receive messages from one or more of the components of the electronic device 100.

The processor 108 may be implemented with any combination of general or special purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The memory 106 may provide instructions and data to the processor 108. The processor 108 may be configured to perform logical and arithmetic operations based on program instructions stored within the memory 106. The instructions in the memory 106 may be executable to implement the methods described herein.

The electronic device 100 shown in FIG. 1 includes a sample behavior analyzer 200. The sample behavior analyzer 200 is shown as receiving sample event data. The sample event data may include event information such as mean fluorescent intensity for an event, event time relative to a point in time for the test (e.g., test start or drop interval), and a delta time. In some implementations, these inputs may be stored in the memory 106. In some implementations, the input is received externally such as via the receiver 102 based on a received message.

The sample behavior analyzer 200 may be configured to generate behavior identification information for the sample or a portion of the sample. One example of behavior identification information is an entrainment factor. The behavior identifier may be based on the received event data where the actual event data is compared to an ideal statistical distribution for the event data. The sample behavior analyzer 200 may be configured to store the generated histogram in the memory 106. Further details of the sample behavior analyzer 200 will be presented in reference to FIG. 2 below.

In some implementations, the behavior identification information may include an actuation control message. The actuation control message may include information identifying the behavior and one or more flow adjustments to improve the sample test behavior.

The electronic device 100 includes a flow controller 600. The flow controller 600 is configured to adjust the cytometric flow for a sample/test. Examples of the adjustments are described below with reference to FIG. 6. The flow controller 600 may receive initiation parameters as a first input. The initiation parameters indicate the initial flow configuration for a sample. The flow controller 600 shown also receives behavior identification information that it may use to adjust the initial flow configuration based on the behavior of the associated sample.

The above described elements of the electronic device 100 may be coupled by a bus 190. The bus 190 may be a data bus, communication bus, or other bus mechanism to enable the various components of the electronic device 100 to exchange information. In some implementations, the bus 190 may facilitate the transfer of power among the elements shown. It will further be appreciated that while different elements have been shown, multiple elements shown may be combined into a single element.

Figure 2:
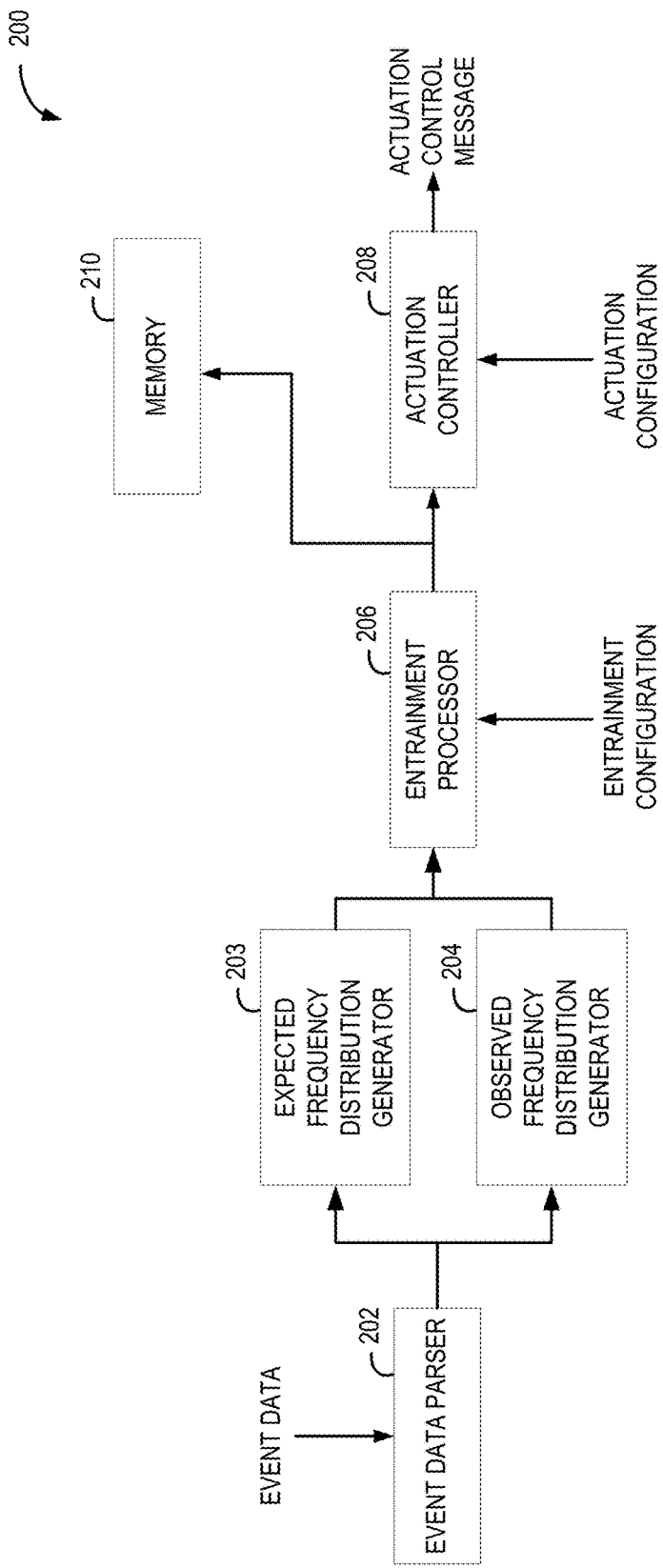
FIG. 2 shows a functional block diagram for one example of a sample behavior analyzer.

FIG. 2 shows a functional block diagram for one example of a sample behavior analyzer 200. The sample behavior analyzer 200 received sample event data as an input. The event data collected by cytometers may vary. For example, some cytometers collect event data at a first level of resolution (e.g., number of bits) while others may collected at a higher resolution. As such, the event data may be more finely represented or include additional information from cytometer to cytometer. Because the sample behavior analyzer 200 may be analyzing event data obtained from various cytometers, the event data is provided to an event data parser 202. Where the sample behavior analyzer 200 is included within a cytometer, the event data format can more reliably be identified. In such implementations, the event data parser 202 may be omitted or combined in another element of the encompassing electronic device.

The event data parser 202 may be configured to determine the format of the even data and provide a standard set of event data for analytical purposes. In some implementations, the event data parser 202 may be configured to augment the received event data. For example, some cytometers may not report the so-called delta time. As such, the event parser 202 may be configured to process the received event data determine the delta time for one or more events included in the data set. The event data may further include the current flow configuration (e.g., rate, time period, etc.).

As shown in FIG. 2, the event data parser 202 may receive a parsing configuration as an input. The parsing configuration may include rules to indicate how to determine what parsing operation(s) are needed. This may be indicated using header fields, event data signatures, or other parsing method. The parsing configuration may further indicate the parsing operation(s) to be performed. For example, a paring configuration may include instructions which may be executed by a processor such as an executable script. The script may specify a series of transformations for the event data to generate the standardized output.

The standardized event data may then be provided to an expected frequency distribution generator 203. The expected frequency distribution generator 203 may be configured to determine the characteristics of a set of events for a well-formed distribution such as a Poisson distribution. The type of distribution may be specified as an input to the expected frequency distribution generator 203 such as via an expectation configuration. The expectation frequency distribution generator 203 may analyze the event data to determine an expected event distribution for the rate and time period of the event data. It will be appreciated that the expected distribution may be identified for a portion of the event data, such as one drop, three drops, thirty drops, or one-sixteenth of a drop.

The standardized event data may also be provided to an observed frequency distribution generator 204. The observed frequency distribution generator 204 may be configured to provide the actual frequency distribution for at least a portion of the event data.

The expected and observed distributions for the sample are then provided to an entrainment processor 206. The entrainment processor 206 is configured to compare the expected and the observed distributions to generate behavior information for the sample. In one implementation, the entrainment processor 206 may take the ratio of expected to observed as discussed above. The comparison implemented by the entrainment processor 206 may be specified using an entrainment configuration input to the entrainment processor 206. The configuration may specify one or more aspects of behavior to analyze and include in the generated behavior information. The configuration may also specify an output format for the behavior information. For example, in an implementation where the sample behavior analyzer 200 is coupled with one or more cytometers, each cytometer may be configured to understand a specific format. Accordingly, the configuration may include static configurations (e.g., combination techniques) as well as dynamic configurations (e.g., target cytometer output format).

The entrainment processor 206 may be configured to then provide the behavior information for further processing. For example, the entrainment processor 206 may store the behavior information in a memory 210. In some implementations, the entrainment processor 206 may utilize the memory 106 included in the electronic device 100 shown in FIG. 1.

The entrainment processor 206 may provide the behavior information to an actuation controller 208. The actuation controller 208 may be configured to identify one or more adjustments to the cytometer based on the behavior information. For example, if the entrainment factor for the sample is high, it may be due to inclusion of a high purity tolerance for the test. The actuation controller 208 may provide a statistical indication of an improved yield for a given reduction in purity. In some implementations, the actuation controller 208 may be configured to automatically generate control messages, such as to reduce the flow rate for the test. The configurations may be specified as an actuation configuration input to the actuation controller 208. The actuation configuration may include rules for adjusting the sorting logic for the test for the analyzed sample events. For example, a rule may specify that up to a 10% reduction in purity is acceptable if it results in a 20% or more increase in yield. In some implementations, the actuation configuration may increase the rate based on detection of an ordered flow and decrease the rate if a disordered flow is detected. Other examples of the adjustments are described below.

Figure 3:
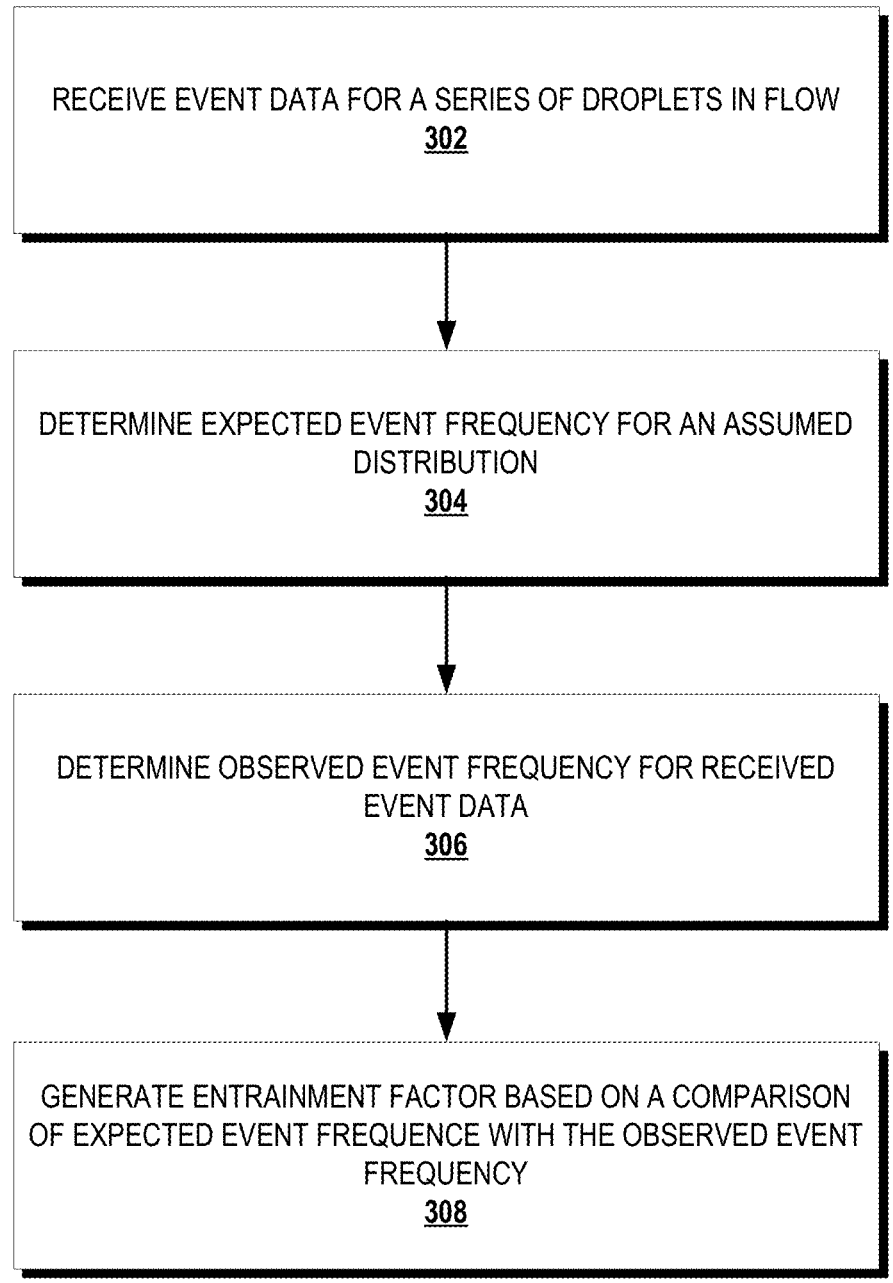
FIG. 3 shows a process flow diagram of an example method of sample behavior analysis.

FIG. 3 shows a process flow diagram of an example method of sample behavior analysis. The process shown in FIG. 3 may be implemented by one or more of the devices described herein such as the electronic device 100 shown in FIG. 1 or the sample behavior analyzer 200 of FIG. 2. The method begins at node 302 where event data for a series of droplets in flow is received. The event data may be received from a flow cytometer during a test. Such provisioning proximate in time from the point of collection to the point of reception may, in some implementations, be referred to as "real-time." While the example shown in FIG. 3 references a droplet as a unit of rate, another unit may be utilized in conjunction with the features described herein.

At node 304, an expected event frequency for an assumed distribution is determined. One non-limiting example of an assumed distribution is a Poisson distribution. The determination may be based on the rate and timer period for at least a portion of the received event data.

At node 306, an observed frequency for the event data is determined. The observed frequency may be determined, in one implementation, based on an application of Equation (1) above.

At node 308, an entrainment factor is generated. The entrainment factor generally describes the behavior of the sample based on the received event data. The entrainment factor may be generated based on a comparison of the expected frequency to the observed frequency. The comparison may be a ratio of the two frequencies. In some implementations, additional factors may be included such as flow configuration, originating cytometer information (e.g., type, model number, firmware version, configuration, and/or the like).

Figure 4:
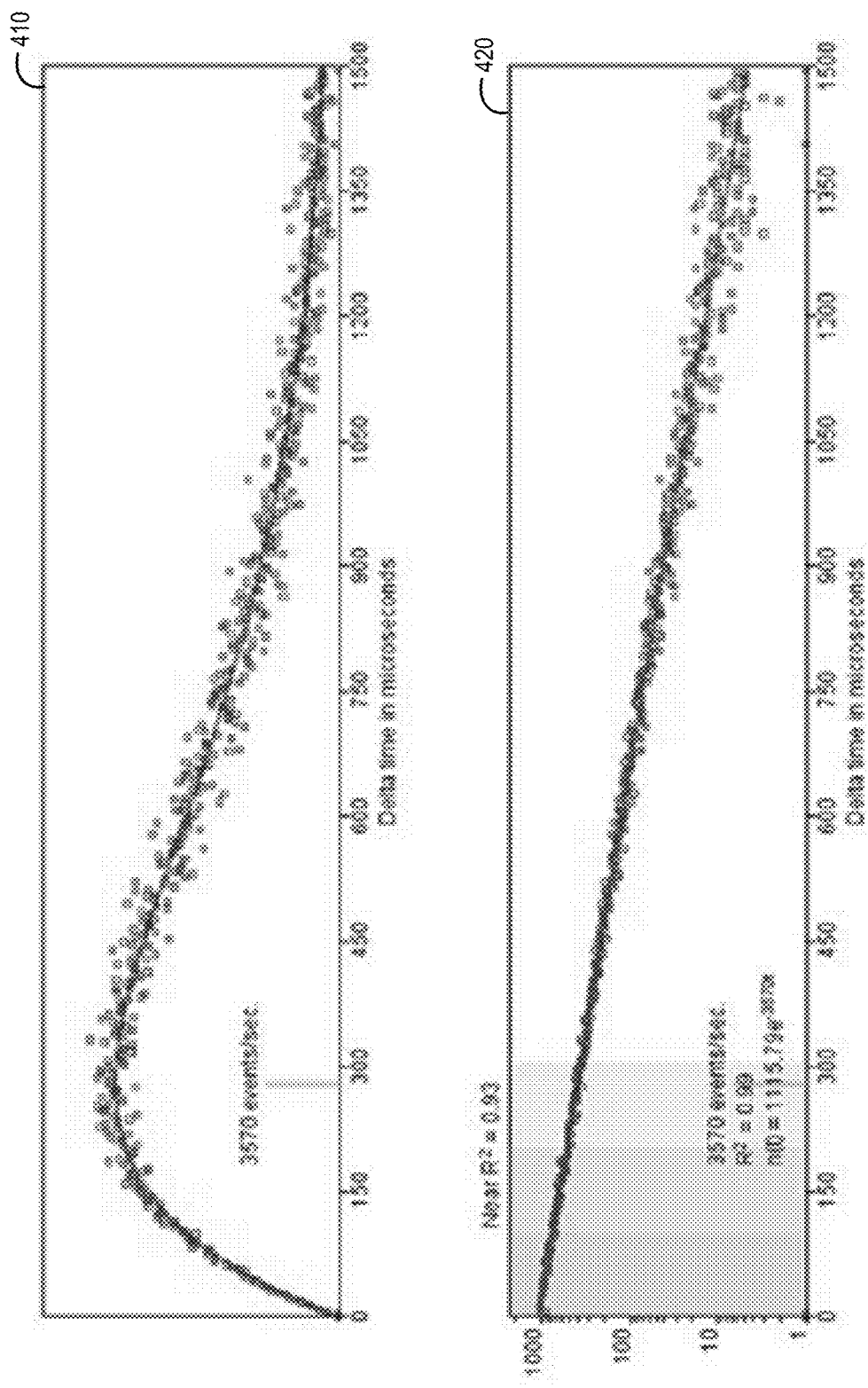
FIG. 4 shows plot diagrams for an example set of event data which does not exhibit dumpiness.

FIG. 4 shows plot diagrams for an example set of event data which does not exhibit dumpiness. Using the example discussed above, the entrainment factor for the event data shown in FIG. 4 would be near or at 1.0.

A first plot diagram 410 shows, on the x-axis, delta time in microseconds. The y-axis represents the number of events detected for the corresponding delta time. As shown in FIG. 4, very few events are detected with a delta time of zero. The most common delta time (e.g., peak point for the graph) is just under 300 microseconds. A second plot diagram 420 shows the same set of data but in log-scale form. It will be noted that this graph generally exhibits a downward slope as delta time increases.

Figure 5:
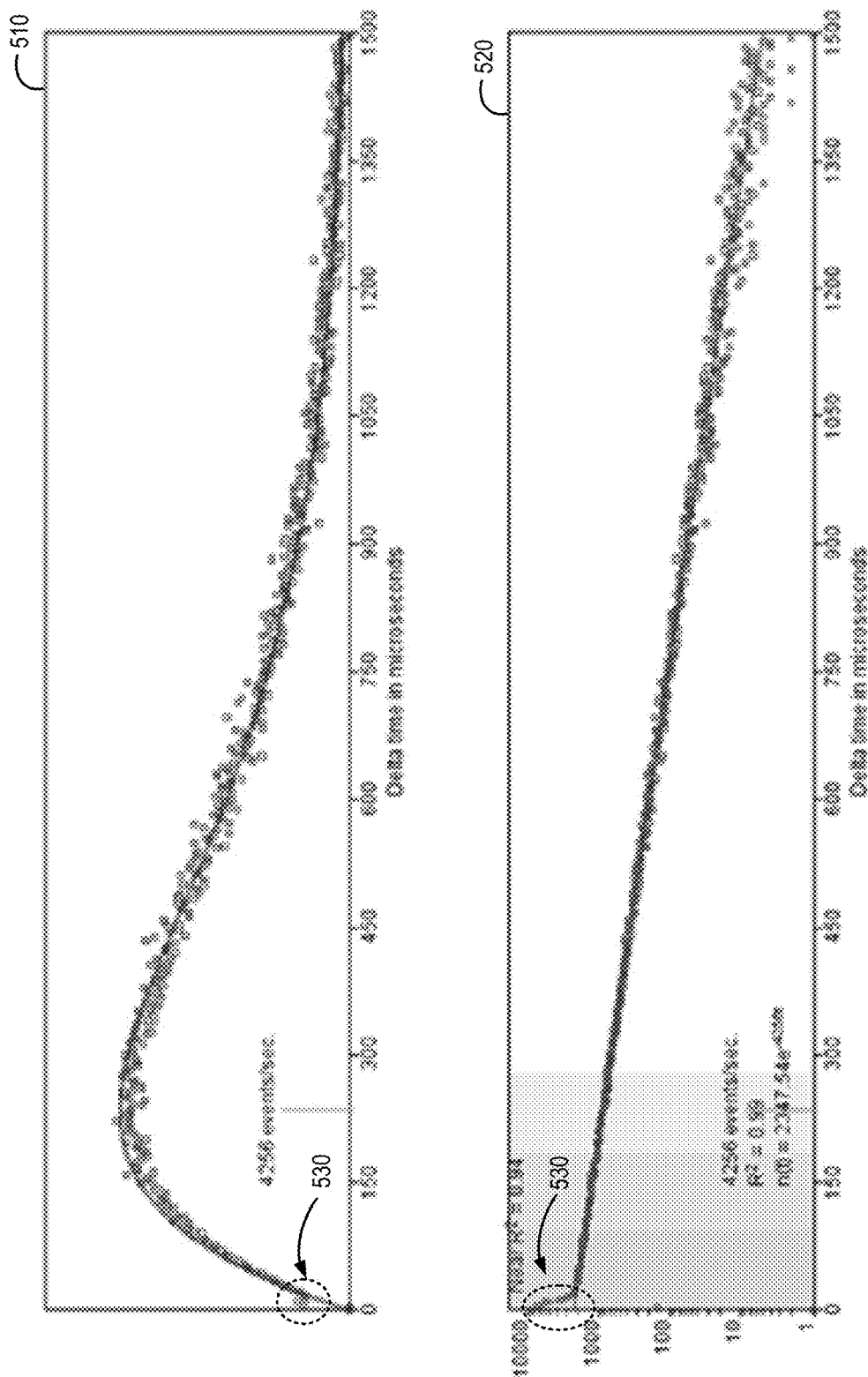
FIG. 5 shows plot diagrams for an example set of event data which exhibits dumpiness.

FIG. 5 shows plot diagrams for an example set of event data which exhibits dumpiness. The event data shown in FIG. 5 represents a less well behaved sorted sample with an entrainment factor near 4.0.

A first plot diagram 510 shows, on the x-axis, delta time in microseconds. The y-axis represents the number of events detected for the corresponding delta time. As shown in FIG. 5, the most common delta time is about 225 microseconds. This shift in FIG. 5 from the set shown in FIG. 4 can be attributed to clumping in the set in FIG. 5.

The shift becomes more apparent when comparing a second plot diagram 520 to the second plot diagram 420. As with the second plot diagram 420, the second plot diagram 520 shows the event data of the first plot diagram 510 in log-scale form. An initial group of events 530 are detected with delta times near zero. This group 530 is missing from the set shown in FIG. 4.

Figure 6:
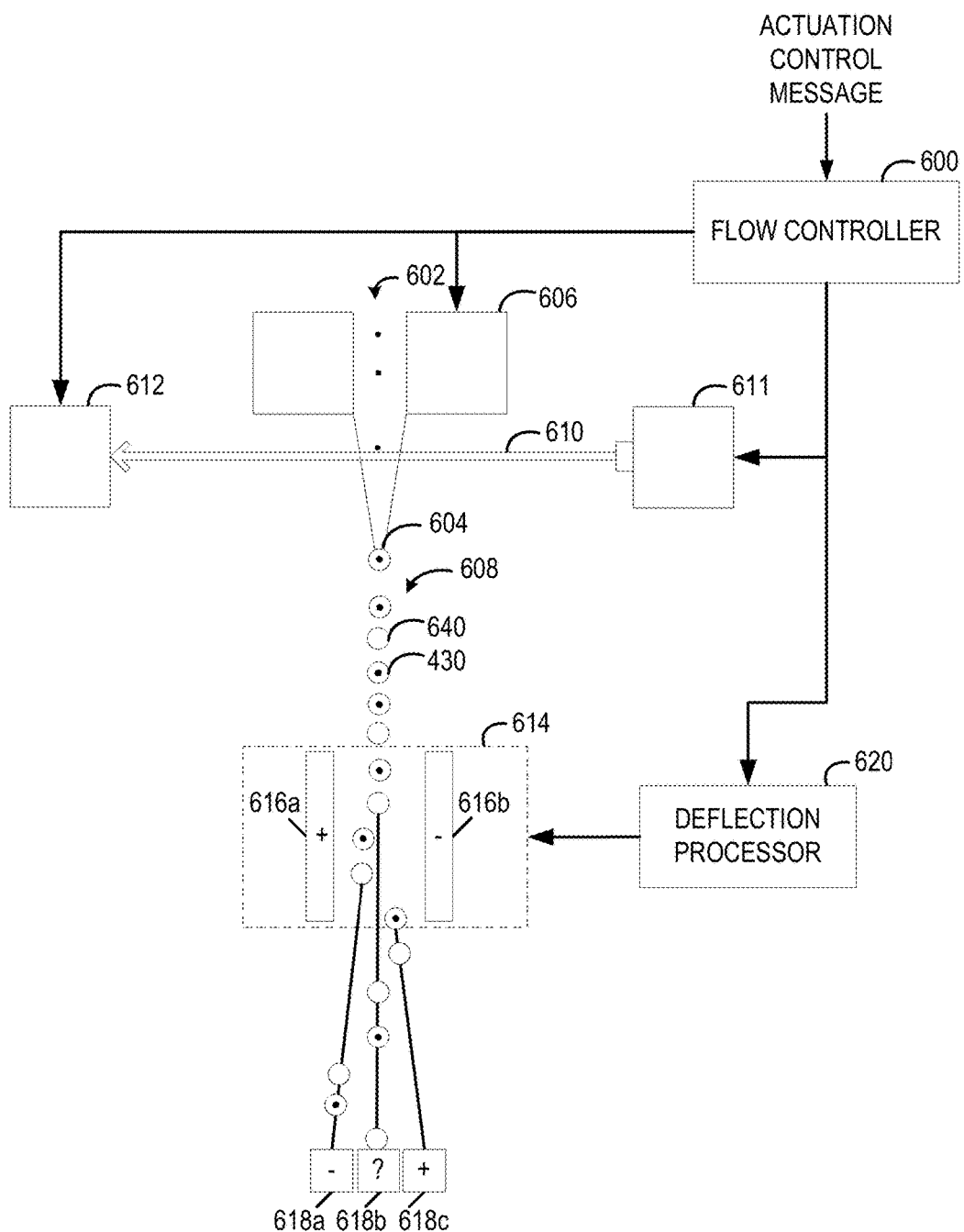
FIG. 6 shows a functional block diagram for one example of a sorting device including an entrainment factor feedback flow controller.

FIG. 6 shows a functional block diagram for one example of a sorting device including an entrainment factor feedback flow controller. The sorting device illustrated in FIG. 6 may be referred to as stream-in-air sorting system. This and other sorting devices are described in U.S. Pat. No. 8,140,300 which is commonly owned and assigned, the disclosure of which is incorporated by reference in its entirety.

Particles in sample stream 602 are shown. The sample stream 602 passes through an orifice 604 of a nozzle 606. The sample stream 602, upon exiting the nozzle 606 forms a jet 608. A laser beam 610 is generated by a laser 611 to illuminate the particles that may be included in the jet 608. The light is detected by a detection station 612 to generate multiple signals that are processed to generate a multiparameter event data point. The generated event data may be provided to a sample behavior analyzer. The providing may be direct, via communication intermediaries (e.g., network/cloud), via memory, or a hybrid configuration.

Based on the values of the multiple signals, prior to droplets leaving jet 608, they are positively charged, negatively charged, or left neutral. Some droplets will include a particle of the sample as shown by a droplet 630 while other droplets will not include a particle of the sample as shown by a droplet 640. Droplets pass through a deflection field 614. The deflection field 614 includes two oppositely charged deflection plates 616a and 616b. The deflection plates 616a and 616b are configured to steer charged droplets in the jet 608 to their respective collection vessels 618a, 618b, or 618c. As shown, vessel 618b collects negatively charged droplets because the positive deflection plate 616a will attract negatively charged droplets. Similarly, vessel 618c will collect positively charged droplets because the negatively charged deflection plate 616b will attract positively charged droplets.

In one collection scheme, the flow system identifies all particles of interest as they pass the detection station 612 based on the values of their signals, and then causes jet 608 to be charged or neutral at the instant the particle of interest leaves jet 608 as a droplet. In this way, particles of interest are caused to have the same charge. This allows collection of the particles in the same collection vessel.

Occasionally multiple particles pass the detection station 612 in close proximity (e.g., clumping). As discussed, entrained events produce signals that may not be distinguishable by the flow system. Such coincident events are generally undesirable and can lead to rejection of the droplet containing the particle of interest. Such rejection can impact the yield of the sort (e.g., number of cells positively identified as a cell of interest).

Figure 7:
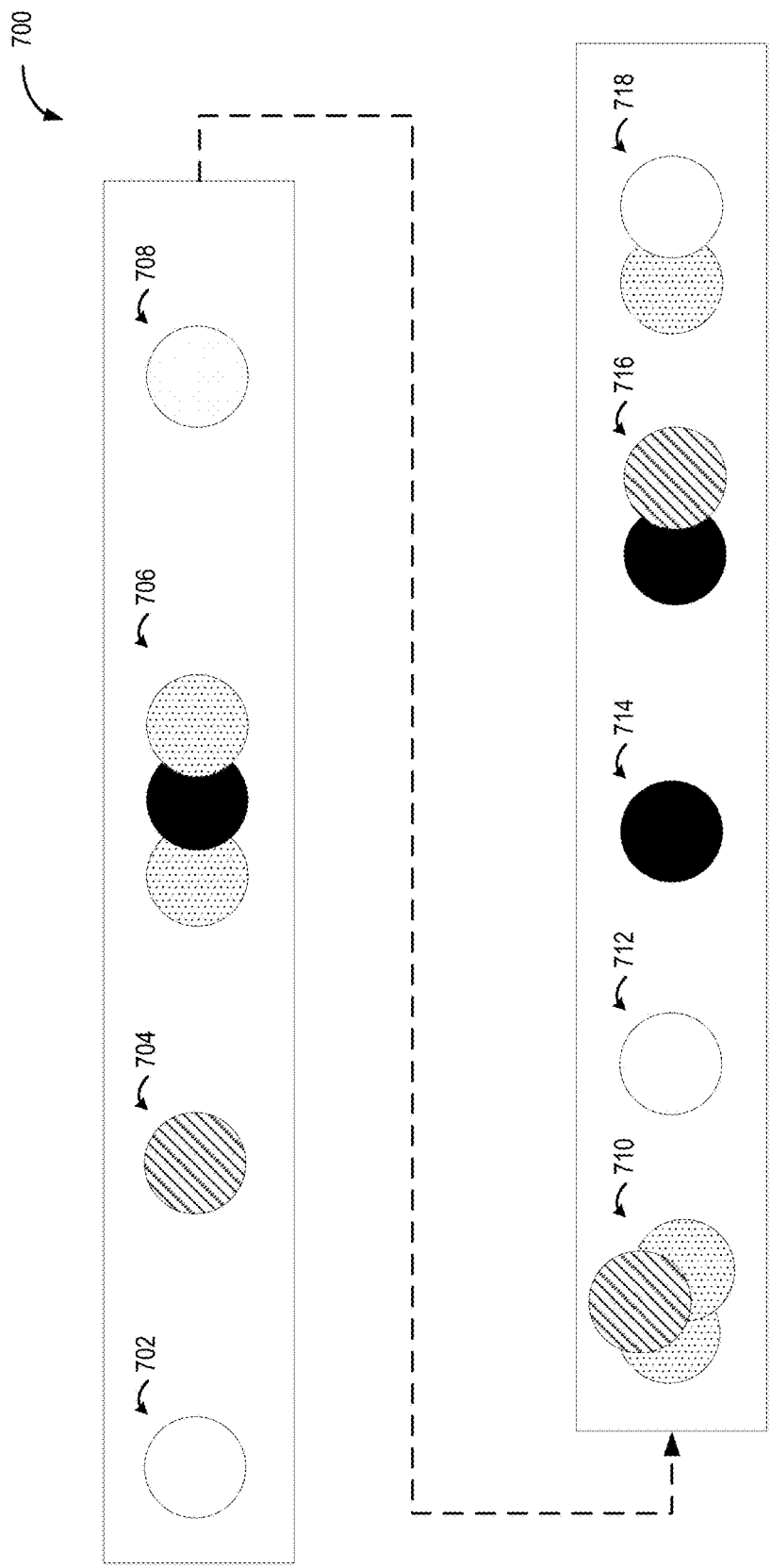
FIG. 7 shows a reconstruction of event distribution in a portion of a stream which illustrates how the particles may be distributed within the portion of the stream.

FIG. 7 shows a reconstruction of event distribution in a portion of a stream which illustrates how the particles may be distributed within the portion of the stream. The stream 700 for the example test shown generally includes four types of particles, target classification particles, abort classification particles, unclassified particles, and particles which experienced an error during classification. The particles may appear alone or, in some circumstances, as clumps. In FIG. 7, a first set of particles 702 including just one particle of the target classification is shown. Continuing down the stream, a second set of particles 704 is shown including just one particle of the abort classification. A third set of particles 706 is shown including two unclassified particles and one error particle. The third set of particles 706 may be considered clumpy (e.g., entrained). A fourth set of particles 708 including one target particle is shown next in the stream 700. As can be seen thus far, as the stream progresses so does time. The first portion of the stream 700 including sets 702, 704, 706, and 708 may represent events appearing in a single droplet. The time between the arrival of the first target particle (e.g., set 702) and the second target particle (e.g., set 704) may be used to characterize the delta time.

The stream 700 continues with a fifth set of particles including two unclassified particles and one abort classification particle. A set 712 including a target classification particle and another set 714 including an error particle follow. A set 716 includes an abort particle and an error particle. In this case, the sorting may be configured to disregard the set 716 as it includes an error. In some implementations, where the sorting bias is adjusted such as based on the sample behavior analysis, the sorting may be configured to sort the set to the aborted collection container. A similar logic may be applied to a final set shown in FIG. 7, set 718. The set 718 includes one unclassified particle and one target particle. For high purity sorting, this set 718 may be directed away from the target collection vessel even though it includes the target particle. For high yield sorting, the set 718 may be directed to the target collection vessel. The stream 700 is simply an example of how particles may flow through the sorting device shown in FIG. 6. The space between sets may be greater or less than shown. Furthermore, there may be more or fewer classifications for particles depending on the test being performed.

The flow controller 600 receives one or more actuation messages. The flow controller 600 may receive one or more actuation control messages from the behavior analyzer. Based on a received actuation control message, the flow controller may adjust one or more elements of the cytometer. For example, the flow controller 600 may receive an actuation control message indicating low levels of clumpiness. In these circumstances, the sample may be aligning within the flow medium. In the event of such alignment, the rate of through put may be increased without sacrificing the purity of the sort. Accordingly, the flow controller 600 may adjust the cytometer to increase the pressure on the flow medium and/or sample to increase the rate at which the sample is introduced into a drop.

The actuation messages may be generated by the behavior analyzer based on the provided event data. As shown in FIG. 6, the flow controller 600 is in communication with various elements included in the sorting device. As such, the flow controller 600 may process an actuation message and adjust an operational characteristic of one or more elements. For example, the flow controller may adjust the laser 611 to change a property of the laser beam 612. Examples of properties which may be adjusted include wavelength, timing of illumination, duration of illumination, angle of illumination, spread, and the like.

The flow controller 600 is shown in communication with the nozzle 606. The flow controller may adjust one or more characteristic of the nozzle 606 such as the size of the orifice, the pressure of either or both of the sample particles or the fluid in which the particles will be included to form droplets, or the charge to be applied to droplets.

The flow controller 600 is shown in communication with a deflection processor 620. The deflection processor 620 is configured to control the charge delivered by the deflection plates 616a and 616b. The flow controller 600 may be configured to provide information to the deflection processor 620 to adjust the charge based on the sample behavior. For example, the strength of a charge may be adjusted such that one or both plates have higher or lower levels of attraction. In a test where purity is important, the strength may be precisely calibrated to attract only those particles of interest. However, if yield is important at the expense of a lower purity, the charge may be increased to allow the sorting more particles.

The flow controller 600 is shown in communication with the detection station 612. The operation of the detection station 612 can be adjusted by the flow controller 600 in response to a received actuation control message. For example, the timing of detection, the resolution of detection, or the area of detection may be adjusted. By adjusting the detection to a less rigorous scheme, the speed at which the detection station 612 can operate may be increased due to the reduced complexity of information processing performed. This can provide another non-limiting advantage of reducing the power resources consumed during sample processing.

It will be understood that the flow controller 600 may adjust multiple elements concurrently. For example, the rate may be adjusted by actuating the nozzle 606 while also adjusting the deflection processor 620. Adjusting the rate may also necessitate the adjustment of the detection station 612 to ensure the event data is captured for the new flow rate. It will also be understood that the flow controller 600 may adjust other elements included in the cytometer based on the actuation control message such as acoustic focusing.

The adjustments by the flow controller 600 based on an actuation control message provides a way for sample behavior as expressed, for example, in delta time to impact operational characteristics of the cytometer. Conditions such as within the instrument, for the sample, and for the flow medium, may vary during the test for a sample. As these conditions change, the delta time characteristics may change. Accordingly, the flow controller 600 may be configured to perform adjustments throughout the sample test. In one instance, the operational characteristics related to sorting may be dynamically adjusted for a sample as the sample is undergoing testing.

Figure 8:
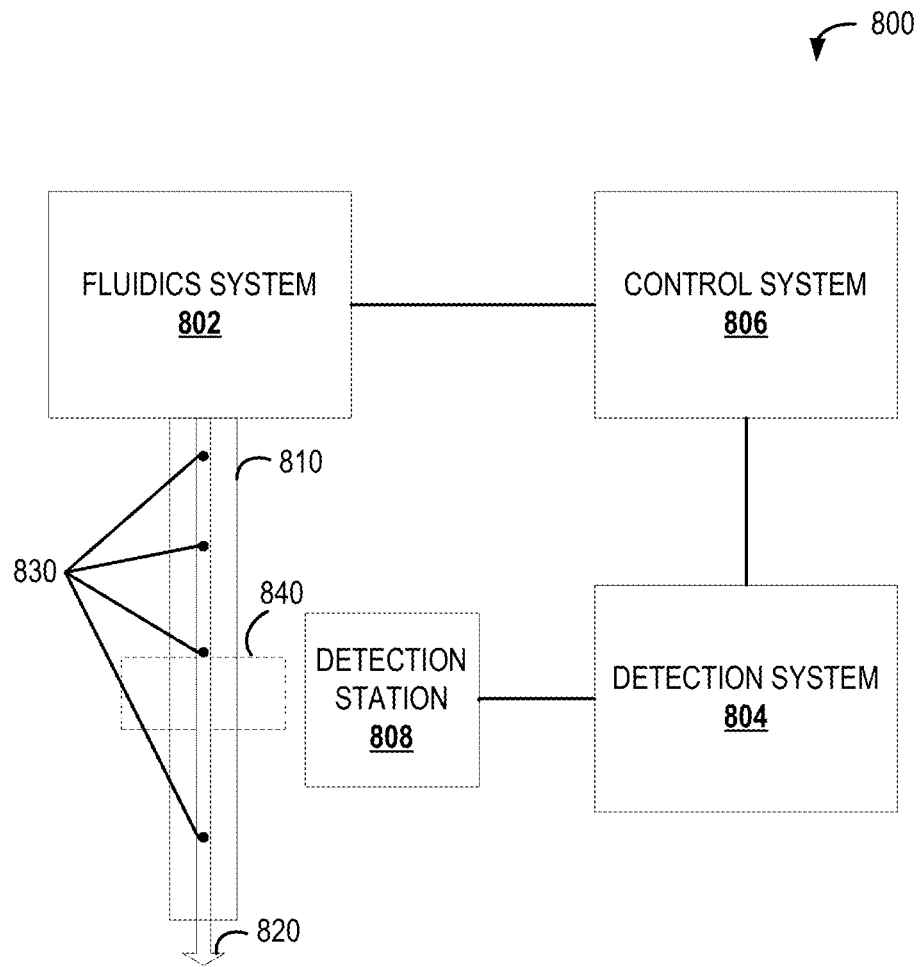
FIG. 8 shows a functional block diagram of a flow system for providing a sample entrainment factor.

FIG. 8 shows a functional block diagram of a flow system for providing a sample entrainment factor. The flow system 800 shown in FIG. 8 may be configured to perform, in whole or in part, the methods described herein such as, for example, the method of FIG. 3. The flow system 800 includes a fluidics system 802. The fluidics system 802 may include or be coupled with a sample tube 810 and a moving fluid column within the sample tube in which particles 830 of a sample move along a common sample path 820.

The flow system 800 includes a detection system 804 configured to collect a signal from each particle as it passes one or more detection stations along the common sample path. A detection station generally refers to a monitored area 840 of the common sample path. Detection may, in some implementations, include detecting light or other property of the particles 830 as they pass through the monitored area 840. In FIG. 8, one detection station 808 with one monitored area 840 is shown. Some implementations of the flow system 800 may include multiple detection stations. Furthermore, it may be desirable for a detection station to monitor more than one area.

Each signal is assigned a signal value to form a data point for each particle. As described above, this data may be referred to as event data. The detection system 804 is configured to collect a succession of such data points in a first time interval.

The flow system 800 also includes a control system 806. The control system 806 shown is operationally associated with the fluidics system 802. The control system 806 configured to generate a calculated signal frequency for at least a portion of the first time interval based on a Poisson distribution and the number of data points collected by the detection system 804 during the first time interval. The control system 806 is further configured to generate an experimental signal frequency based on the number of data points in the portion of the first time interval. The control system 806 additionally compares the experimental signal frequency with that of a calculated signal frequency or a predetermined signal frequency. The control system 806 then provides an entrainment factor for the sample. The entrainment factor is based at least in part on a result of the comparing.

The behavior information (e.g., entrainment factor) can be used to further process cytometric event data. In one implementation, the entrainment factor may be used to adjust the resulting cell counts. For example, the entrainment factor may be combined with the clumpy cell count to provide an adjusted cell count which, statistically speaking, reflects an expected count for the sample.

In one implementation, the entrainment factor may be used to gate the events for a sample. For example, a subpopulation of interest having an entrainment factor may be provided identified. In some circumstances, the dumpiness may be used as an indicia of certain diagnostic conditions.

In a further implementation, the entrainment factors for tests for a cytometer may be tracked over time. Over time, the level of entrainment may change based on a variety of conditions which may be attributed to the cytometer. Where the entrainment information is tracked over time, a trend may be identified whereby the level of clumping in increasing for the cytometer. The increase may be an increase as compared to similar model cytometers, increase as compared to an average for the cytometer, or other comparison metric. Upon exceeding a configurable threshold, the cytometer may provide an indication that maintenance is needed to address the clumping. Such maintenance may include cleaning, recalibration, or other corrective action which can reduce the clumping for samples. In some implementations, the maintenance may be automatically performed such as by a processor configured to monitor entrainment over time and perform the above mentioned comparisons.

One implementation may include the features described to predict sorting performance for a population. For example, the inverse of the average population delta-time may be used as an average virtual rate estimate to predict sorting performance for that population and thereby provide information which can be used to optimize sorting logic for that population based upon its measured behavior. In an embodiment, a matrix may be generated, such as by the sample behavior analyzer 200 or the processor 108, to assess yield (efficiency) and purity outcomes for a classified population p. The matrix may be generated based on average virtual rates computed from the inverse of the average delta-times. One example, which is a modification of Equation (1), is shown in Equation (3).

$$Efficiency_p = e^{-\left(\frac{1}{delta\ time_p} \times (1-fraction_p) \times \frac{d}{f}\right)} \quad (3)$$

Some implementations may include selective anti-coincidence logic. The sorting logic may adjust how the behavior is analyzed. For example, if with standard anti-coincidence logic enabled the logical drop packet d is 1.5 drops in "purity" mode, and 1.0 drops in a "yield" mode (to incrementally decrease the number of potential aborts). Some implementations may include an "enrich" mode with anti-coincidence disabled which can provide a 1.0 drops. The matrix may be generated to assess the sorting performance of multiple populations with differing average delta-times within a sample under the different sorting modes such as pure, yield, and enrich. While the discussion uses pure, yield, and enrich as the example sorting logics, fewer or more sorting logics associated with different logical drop packets and/or other sorting parameters may be used to assess the sorting performance in conjunction with delta-times.

Furthermore, the estimates from measured delta-times may be used to compare predicted performance from average delta-times contrasted to that predicted if the population were homogenous Poisson in its behavior. This information is a further example of sample behavior information.

Consider a PBMC sample stained for CD4, CD19, and CD14 cell surface markers where the average rate is 6400 events per second and the drop rate is 39200 Hz. The four populations to be sorted are CD4+ (37.13%), CD4− (13.85%), CD19+ (10.97%), and CD14+ (1.83%). The average expected efficiency (yield) would be between approximately 79% and 85% yield in "purity" mode with a 1.5 drop purity check and between 85% and 90% in "yield" mode with a 1.0 drop purity check. Table 1 summarizes the estimated yield using standard method (e.g., not considering delta-time).

TABLE 1

| | | estimated yield (standard method) | | |
|---|---|---|---|---|
| Population | % Total | purity | yield | enrich |
| CD4+ | 37.13% | 85.74% | 90.25% | 100.00% |
| CD4− | 13.85% | 80.99% | 86.89% | 100.00% |
| CD19+ | 10.97% | 80.42% | 86.48% | 100.00% |
| CD14 | 1.83% | 78.64% | 85.20% | 100.00% |

However, the observed yield from the CD14 population in purity mode during the sort was nearer to 33% as opposed to the expected 79%. The experimental results can be predicted by the average (median) delta-time of the CD14+ population. Table 2 summarizes the estimated yield using the delta-time method.

TABLE 2

| | delta time | | estimated yield (delta time method) | | |
|---|---|---|---|---|---|
| Population | (µsec) | % Total | purity | yield | enrich |
| CD4+ | 168.4 | 37.13% | 86.69% | 90.92% | 100.00% |
| CD4− | 171.9 | 13.85% | 82.55% | 88.00% | 100.00% |
| CD19+ | 174.5 | 10.97% | 82.26% | 87.80% | 100.00% |
| CD14 | 33.2 | 1.83% | 32.26% | 47.03% | 100.00% |

Similarly, the expected purity of the population may be estimated by estimating the probability of another particle being in the same drop packet as the classified cell being sorted. The expected purity is yet another example of sample behavior information. The measured variability in estimating particle location can be used as d in Equation (3) to estimate the frequency of error. For the example discussed above, the frequency of error was determined to be 0.2 drops. Using this information, the estimated purity may be generated. Table 3 shows estimated purities for various sorting modes for populations exhibiting a 0.2 drop frequency of error.

TABLE 3

| | estimated purity | | |
|---|---|---|---|
| Population | purity | yield | enrich |
| CD4+ | 99.50% | 97.97% | 91.12% |
| CD4− | 99.50% | 97.23% | 88.41% |
| CD19+ | 99.50% | 97.14% | 88.09% |
| CD14 | 99.50% | 96.85% | 87.11% |

In some implementations, behavior analysis may estimate the frequency of an unwanted passenger cell based on the drop rate. This frequency is a further example of sample behavior information. Equation (4) shows one expression of purity estimate which may be included in the devices and methods described.

$$Purity_{enrich} = \frac{1.0}{\left(1.0 + 1.0 - e^{-\left(Rate \times \frac{1.0 - fraction}{f}\right)}\right)} \quad (4)$$

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as general purposes computers, wireless communication devices, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A method for controlling flow of a flow cytometer sample, the method comprising:
    flowing the sample comprising a series of particles through the flow cytometer wherein each particle is associated with a signal;
    detecting a series of events with a detection system in a first time interval from a stream formed from the flow cytometer;
    calculating an expected frequency of events in the first time interval based on a characterizing distribution;
    measuring, via the flow cytotneter, an observed frequency of events within a second time interval, wherein the second time interval is within the first time interval;
    while particles for the sample are flowing through the flow cytometer, generating an entrainment factor based at least in part on a comparison of the observed frequency to the expected frequency;

determining the entrainment factor indicates a level of sample clumping below a threshold; and controlling the detection system or the stream formed from the flow cytometer based on the determined entrainment factor while particles for the sample are flowing through the flow cytometer.

2. The method of claim 1, wherein the characterizing distribution includes a Poisson distribution.

3. The method of claim 1, further comprising generating at least one of an estimated yield or an estimated purity based on the entrainment factor and a sorting logic.

4. The method of claim 1, wherein controlling the stream comprises:

increasing a flow rate of the stream while particles for the sample are flowing through the flow cytometer.

5. The method of claim 1, wherein the entrainment factor is one of a plurality of entrainment factors calculated during successive time intervals for a flow cytometer sample.

6. The method of claim 1, wherein the sample comprises peripheral blood cells wherein the peripheral blood cells as are comprised of a first and second component labeled with a first and second label.

7. The method of claim 6, wherein the entrainment factor is generated for the first component and another entrainment factor is generated for the second component.

* * * * *